(12) United States Patent
Duan et al.

(10) Patent No.: US 11,511,092 B2
(45) Date of Patent: Nov. 29, 2022

(54) AUTOMATIC DRUG DELIVERY DEVICE

(71) Applicant: Ankon Medical Technologies (Shanghai) Co., LTD., Shanghai (CN)

(72) Inventors: Xiaodong Duan, Pleasanton, CA (US); Lei Liu, Suzhou (CN)

(73) Assignee: Ankon Medical Technologies (Shanghai) Co., LTD, Shanghai (CN)

( * ) Notice: Subject to any disclaimer, the term of this patent is extended or adjusted under 35 U.S.C. 154(b) by 215 days.

(21) Appl. No.: 16/775,749

(22) Filed: Jan. 29, 2020

(65) Prior Publication Data

US 2020/0238063 A1 Jul. 30, 2020

(30) Foreign Application Priority Data

Jan. 29, 2019 (CN) .......................... 201910087366.X

(51) Int. Cl.
*A61M 31/00* (2006.01)

(52) U.S. Cl.
CPC ....... *A61M 31/002* (2013.01); *A61M 2202/04* (2013.01); *A61M 2202/064* (2013.01); *A61M 2210/106* (2013.01); *A61M 2210/1042* (2013.01); *A61M 2210/1053* (2013.01); *A61M 2210/1057* (2013.01); *A61M 2210/1064* (2013.01)

(58) Field of Classification Search
CPC .. A61K 9/0004; A61K 9/0002; A61M 31/002
See application file for complete search history.

(56) References Cited

U.S. PATENT DOCUMENTS

| | | | | |
|---|---|---|---|---|
| 4,410,328 A | * | 10/1983 | Theeuwes | A61K 9/0004 604/892.1 |
| 4,455,145 A | * | 6/1984 | Theeuwes | A61K 9/0004 604/892.1 |
| 4,643,721 A | * | 2/1987 | Brunet | A61M 5/2066 604/191 |
| 4,717,568 A | * | 1/1988 | Eckenhoff | A61K 9/0004 424/468 |
| 4,717,718 A | * | 1/1988 | Eckenhoff | A61M 31/002 424/438 |
| 4,723,958 A | * | 2/1988 | Pope | A61M 31/002 604/890.1 |

(Continued)

*Primary Examiner* — Nathan R Price
*Assistant Examiner* — Mark A Igel
(74) *Attorney, Agent, or Firm* — Treasure IP Group, LLC

(57) ABSTRACT

The present invention provides an automatic drug delivery device. The automatic drug delivery device includes an enclosure and a first piston disposed in the enclosure. The first piston partitions the enclosure to a first drug delivery chamber and a first expansion chamber. A first through hole and a second through hole are formed in the wall of the enclosure, the first through-hole communicates with the first drug delivery chamber, and the second through-hole communicates with the first expansion chamber. A first targeted dissolution membrane covers the first through hole and the second through hole, and dissolves at a first targeted region. A drug is filled in the first drug delivery chamber, and an expandable material is included in the first expansion chamber. The expandable material in the first expansion chamber can expand after absorbing liquid.

11 Claims, 4 Drawing Sheets

(56) References Cited

U.S. PATENT DOCUMENTS

| | | | | |
|---|---|---|---|---|
| 4,729,793 | A * | 3/1988 | Eckenhoff | A61M 31/002 106/162.72 |
| 4,772,474 | A * | 9/1988 | Eckenhoff | A61K 9/0004 424/438 |
| 4,783,337 | A * | 11/1988 | Wong | A61K 9/0004 424/468 |
| 4,837,111 | A * | 6/1989 | Deters | A61P 25/02 424/473 |
| 4,927,633 | A * | 5/1990 | Eckenhoff | A61K 9/0004 424/438 |
| 5,030,216 | A * | 7/1991 | Theeuwes | A61K 9/0004 604/892.1 |
| 5,209,746 | A * | 5/1993 | Balaban | A61K 9/0004 604/892.1 |
| 5,980,508 | A * | 11/1999 | Cardamone | A61M 31/002 604/890.1 |
| 7,655,257 | B2 * | 2/2010 | Peery | A61K 38/09 424/473 |
| 8,021,357 | B2 * | 9/2011 | Tanaka | A61M 5/14248 604/890.1 |
| 2001/0021822 | A1 * | 9/2001 | Ayer | A61K 9/0004 604/148 |
| 2002/0102305 | A1 * | 8/2002 | Faour | A61K 9/209 424/473 |
| 2005/0101943 | A1 * | 5/2005 | Ayer | A61K 9/0004 604/892.1 |
| 2005/0107772 | A1 * | 5/2005 | Chen | A61M 5/145 424/424 |
| 2008/0091176 | A1 * | 4/2008 | Alessi | A61M 5/14276 604/892.1 |
| 2009/0202608 | A1 * | 8/2009 | Alessi | A61K 38/2264 424/424 |
| 2011/0076317 | A1 * | 3/2011 | Alessi | A61P 3/06 424/423 |
| 2012/0059349 | A1 * | 3/2012 | Kuo | A61J 1/067 604/500 |
| 2013/0041353 | A1 * | 2/2013 | Shin | A61K 9/0004 604/892.1 |
| 2014/0088345 | A1 * | 3/2014 | Uhland | A61K 9/0004 600/35 |
| 2014/0088346 | A1 * | 3/2014 | Uhland | A61B 17/43 600/35 |
| 2016/0279399 | A1 * | 9/2016 | Lee | A61M 31/002 |
| 2018/0036522 | A1 * | 2/2018 | Davey | A61K 38/28 |

* cited by examiner

AUTOMATIC DRUG DELIVERY DEVICE

CROSS-REFERENCE OF RELATED APPLICATIONS

The application claims priority to Chinese Patent Application No. 201910087366.X filed on Jan. 29, 2019, the contents of which are incorporated by reference herein.

FIELD OF INVENTION

The present invention relates to a medical device, and more particularly to a automatic drug delivery device.

BACKGROUND

With the development of science and technology, increasing drugs have been developed for the treatment of various diseases. Traditional orally taken drugs, for example, medicine powders or a medicine solutions, are generally sugar-coated or have an outer coating of capsules. After the drugs reach stomach, the outer coating can be dissolved by gastric juice and the content released.

However, using the drug delivery method, the sugar coating can dissolve as the drug enters stomach, so the powder inside cannot reach a specific region. In addition, after the sugar coating is dissolved, the drug may completely enter the digestive tract at one time, which is not conducive to the absorption of drug.

SUMMARY OF THE INVENTION

The present invention provides an automatic drug delivery device. The automatic drug delivery device can automatically release drug at a targeted region without an external power source, and can better control the drug release rate.

The present invention provides an automatic drug delivery device, comprising:
  an enclosure and a first piston disposed in the enclosure, wherein the first piston partitions the enclosure to a first drug delivery chamber and a first expansion chamber;
  a first through hole and a second through hole formed in the wall of the enclosure, wherein the first through-hole communicates with the first drug delivery chamber, and the second through-hole communicates with the first expansion chamber;
  a first targeted dissolution membrane, which covers the first through hole and the second through hole and dissolves at a first targeted region;
  a drug filled in the first drug delivery chamber; and
  an expandable material provided in the first expansion chamber, that can expand after absorbing liquid.

Further, the expansion rate of the expandable material that absorbs liquid and/or the size of the second through hole are controlled to adjust the rate of the first piston compressing the first drug delivery chamber, so as to control the drug release rate.

Further, the automatic drug delivery device further comprises:
  a second drug delivery chamber;
  a second piston provided between the first drug delivery chamber and the second drug delivery chamber, wherein the first drug delivery is disposed in a side of the second drug delivery chamber opposite the first expansion chamber;
  a third through hole communicating with the second drug delivery chamber;
  a second targeted dissolution membrane covering the third through hole that dissolves at a second targeted region; and
  drugs filled in both the first drug delivery chamber and the second drug delivery chamber.

Further, the third through hole is formed in the second piston, and the third through hole communicates with the second drug delivery chamber.

Further, the third through hole is formed in the wall of the enclosure, and when the drug in the first drug delivery chamber is released, the third through hole communicates with the second drug delivery chamber.

Further, the automatic drug delivery device further comprises:
  a second expansion chamber;
  an expandable material disposed in the second expansion chamber, that expands after absorbing liquid;
  a third piston provided between the first expansion chamber and the second expansion chamber;
  a fourth through hole that is covered by the second targeted dissolution membrane; and wherein when the drug in the first drug delivery chamber is released, the third through hole communicates with the second drug delivery chamber and the fourth through hole communicates with the second expansion chamber.

Further, both the third through hole and the fourth through hole are formed in the wall of the enclosure.

Further, the expandable material is water swellable sponge, sodium polyacrylate-modified lignocellulose, chitosan-modified lignocellulose, or a polymer mixed by rubber polymer with water-absorbing resin.

Further, the first targeted dissolution membrane and the second targeted dissolution membrane are selected from a mixture of EUDRAGIT L100-55 and EUDRAGIT Plastoid B, pectin, guar gum, or a mixture of EUDRAGIT S100 and EUDRAGIT Plastoid B.

Further, the enclosure is made of one or more of medical grade polycarbonate, polyurethane, polyacrylate, polymethyl methacrylate, polyetheretherketone, polystyrene and polyethylene.

In summary, the present invention provides a piston, an expandable material and a targeted dissolving material, which are arranged to enable the targeted dissolution membrane to dissolve at a targeted region and then the expandable material absorbs liquid to expand and push the piston to release the drug at a targeted position. The automatic drug delivery device can automatically release drug at a targeted region without an external power source, and can better control the drug release rate.

The above description is only an overview of the technical solutions of the invention. For a thorough understanding of the technical means of the invention, and implementation in accordance with the specification, and that the above-described and other objects, features and advantages of the invention can be more clearly understood, detailed description of the preferred embodiments can be described in detail with reference to the accompanying drawings.

DETAILED DESCRIPTION

The present invention can be described in detail below with reference to the accompanying drawings and preferred embodiments.

The present invention provides an automatic drug delivery device. The automatic drug delivery device can automatically release drug at a targeted region without an external power source, and can better control the drug release rate.

Figure 1:
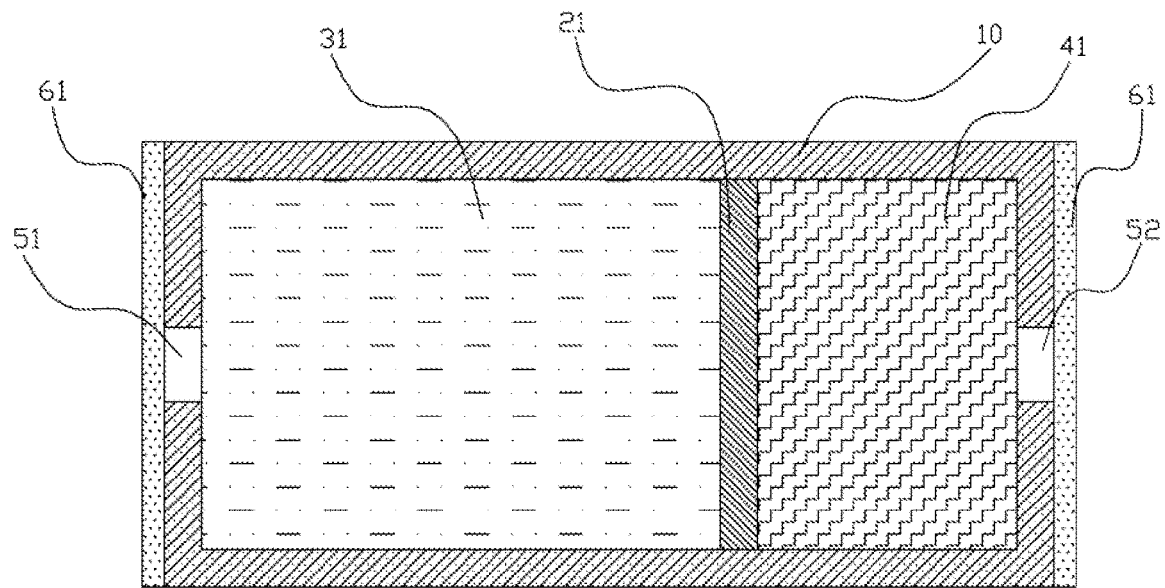
FIG. 1 shows a structural view of an automatic drug delivery device according to the first embodiment of the present invention.
Figure 2:
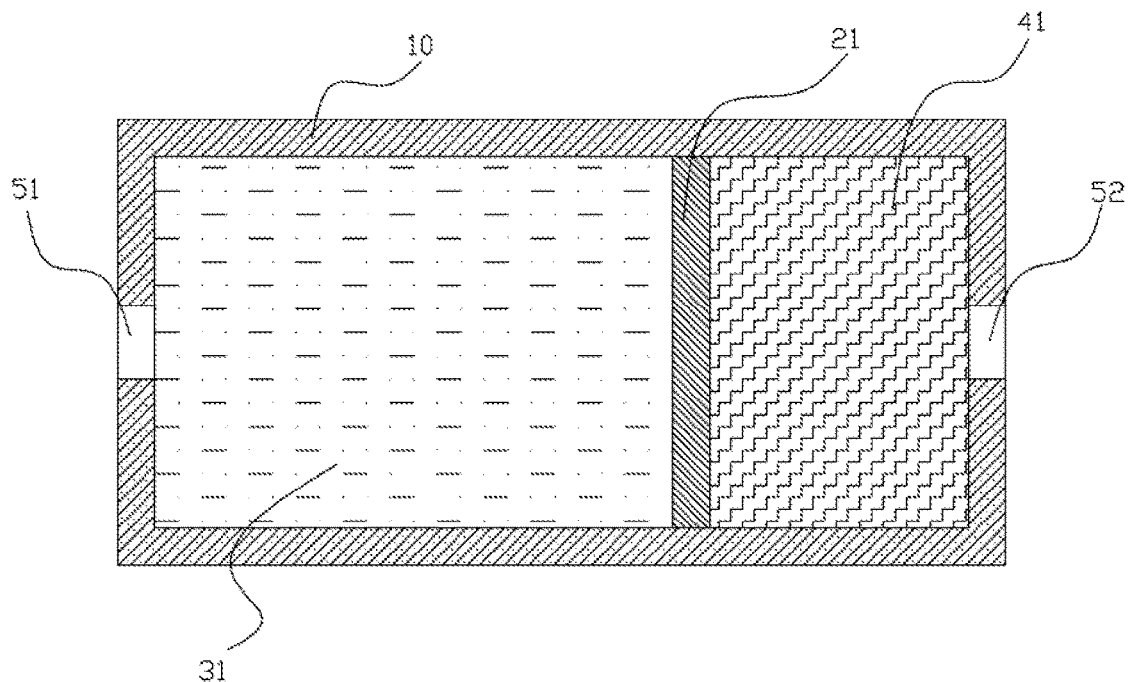
FIG. 2 shows a structural view of the automatic drug delivery device of FIG. 1 after membranes are dissolved.
Figure 3:
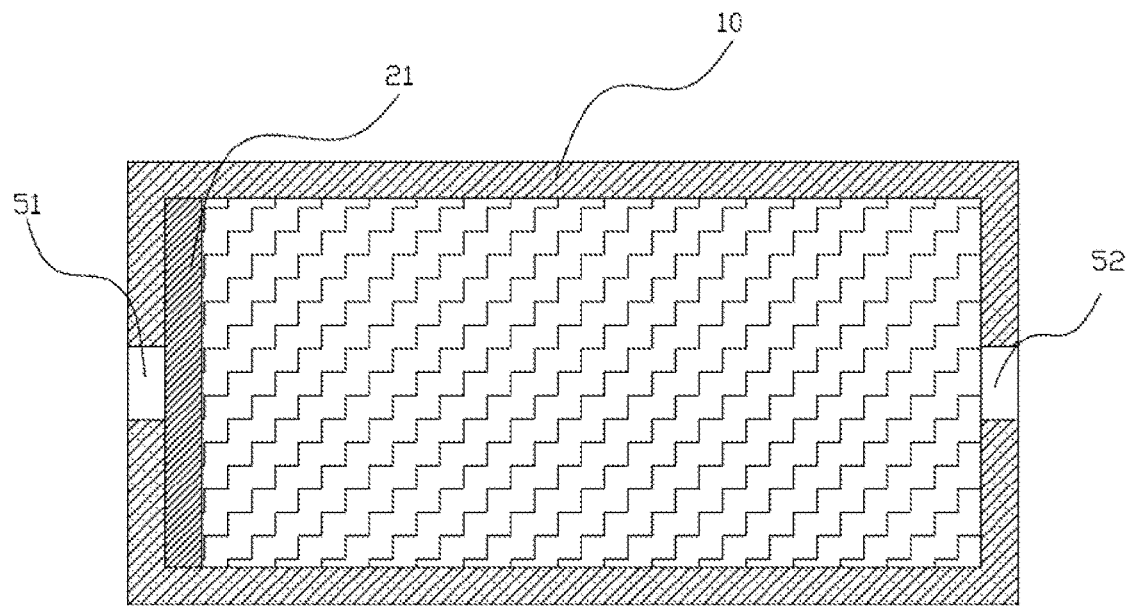
FIG. 3 shows a structural view of the automatic drug delivery device of FIG. 1 after drugs in the first drug delivery chamber have been released.

FIG. 1 shows a structural view of an automatic drug delivery device according to the first embodiment of the present invention. FIG. 2 shows a structural view of the automatic drug delivery device of FIG. 1 after membranes are dissolved. FIG. 3 shows a structural view of the automatic drug delivery device of FIG. 1 after drugs in the first drug delivery chamber have been released. Referring to FIGS. 1-3, the present invention provides an automatic drug delivery device, and the automatic drug delivery device comprises an enclosure 10 and a first piston 21. The first piston 21 is disposed in the enclosure 10 to partition the enclosure 10 to a first drug delivery chamber 31 and a first expansion chamber 41. The enclosure 10 comprises a first through hole 51 and a second through hole 52 formed in the wall of the enclosure 10. The first through hole 51 communicates with the first drug delivery chamber 31, and the second through hole 52 communicates with the first expansion chamber 41. A first targeted dissolution membrane 61 covers the first through hole 51 and the second through hole 52, that dissolves at a first targeted region. The first drug delivery chamber 31 is filled with a drug, and the drug can be, but is not limited to, a medicine powder or a medicine solution. The first expansion chamber 41 comprises an expandable material, that can expand after absorbing liquid. The size of the first targeted dissolution membrane 61 is preferably capable of covering the corresponding first through hole 51 or the second through hole 52. For example, the first targeted dissolution membrane 61 is 0.1-1 cm larger than the corresponding through hole at each angle. Referring to FIG. 2, a cross-section of the automatic drug delivery device has a vertical dimension and horizontal dimension. The horizontal dimension is longer than the vertical dimension. The enclosure of the automatic drug delivery device continuously covering surface areas of the automatic drug delivery device along both the horizontal dimension and vertical dimension. The first through hole 51 and the second through hole 52 The first through hole 51 and the second through hole 52 have a length dimension along the vertical dimension of the automatic drug delivery device, the length of the through holes is substantially less than the enclosure along with the same vertical dimension.

In the embodiment, the first piston 21 is disposed in the enclosure 10 to partition the enclosure 10 to the first drug delivery chamber 31 and the first expansion chamber 41, drugs are filled in the first drug delivery chamber 31 and the expandable material is filled in the first expansion chamber 41, and the first through hole 51 and the second through hole 52 that communicate with the first drug delivery chamber 31 and the first expansion chamber 41 are covered by the first targeted dissolution membrane 61 that dissolves at a targeted region. After the automatic drug delivery device is taken through the digestive tract and reaches a targeted region in the digestive tract, due to the special environment of the targeted region, such as pH value, special flora and/or specific enzyme, the targeted dissolution membrane is dissolved (as shown in FIG. 2), so that the first drug delivery chamber 31 and the first expansion chamber 41 communicate with the targeted region through the first through hole 51 and the second through hole 52. The targeted region can be, but is not limited to, the stomach, duodenum, jejunum, or colon. Liquid at the targeted region can enter the first expansion chamber 41 through the second through hole 52. The expandable material absorbs the liquid and expands, and then pushes the first piston 21 in a direction to the first drug delivery chamber 31. The first piston 21 compresses the drug and releases it to the targeted region through the first through hole 51. Therefore, an automatic drug delivery without an external power source is realized. Further, since it takes a process for the expandable material to absorb liquid and expand, the expansion rate of the expandable material that absorbs liquid and/or the size of the second through hole 52 are controlled to control the rate of the first piston 21 compressing the first drug delivery chamber 31, so as to control the drug release rate.

More specifically, in the embodiment, the enclosure 10 can be made of one or more of medical grade polycarbonate, polyurethane, polyacrylate, polymethyl methacrylate, polyetheretherketone, polystyrene, and polyethylene. The shape of the enclosure 10 is not limited, and it can be cylinder-shaped, capsule-shaped, or made to other shapes suitable for swallowing.

The first piston 21 can be made of one or more of styrene-butadiene rubber, ethylene-propylene-diene rubber, silicone rubber, polyurethane rubber, and nitrile rubber.

In the embodiment, the material of the first targeted dissolution membrane 61 that dissolves at a targeted region can be determined according to the targeted region. For example, when duodenum is the targeted region, the first targeted dissolution membrane 61 can resist the erosion of acidic liquid in the stomach and dissolve in the duodenum due to high pH to release the drug, for example, the material of the first targeted dissolution membrane 61 can be a compound of EUDRAGIT L100-55 and EUDRAGIT Plastoid B. When colon is the targeted region, the first targeted dissolution membrane 61 can dissolve due to the glycosidases and glycanase produced by special flora in colon to release the drug, for example, the material of the first targeted dissolution membrane 61 can be pectin and/or guar gum. In another embodiment, when colon is the targeted region, the first targeted dissolution membrane 61 can dissolve in the colon due to high pH to release the drug, for example, the material of first targeted dissolution membrane 61 can be a compound of EUDRAGIT S100 and EUDRAGIT Plastoid B. In the embodiment, in order to ensure that the first targeted dissolution membrane 61 of the automatic drug delivery device can dissolve at the targeted region, the thickness of the first targeted dissolution membrane 61 can be 100 nm-100 µm.

In the embodiment, the expandable material can be a water absorbing sponge, for example, medical polyvinyl alcohol (PVA) sponge, polyurethane (PU) sponge, cotton fiber sponge, lignocellulose sponge, and/or chitosan sponge. The expandable material can also be sodium polyacrylate-modified lignocellulose, chitosan-modified lignocellulose, or a polymer mixed by rubber-based polymer with water-absorbent resin. The mixture of a rubber-based polymer and a water-absorbent resin may be Polyether-modified polyurethane, sodium polyacrylate-modified styrene-butadiene rubber, polytetrahydrofuran-modified butadiene rubber, and/or acrylamide-modified ethylene-propylene rubber. The type, volume, and expansion rate of rubber can be set as required.

Figure 4:
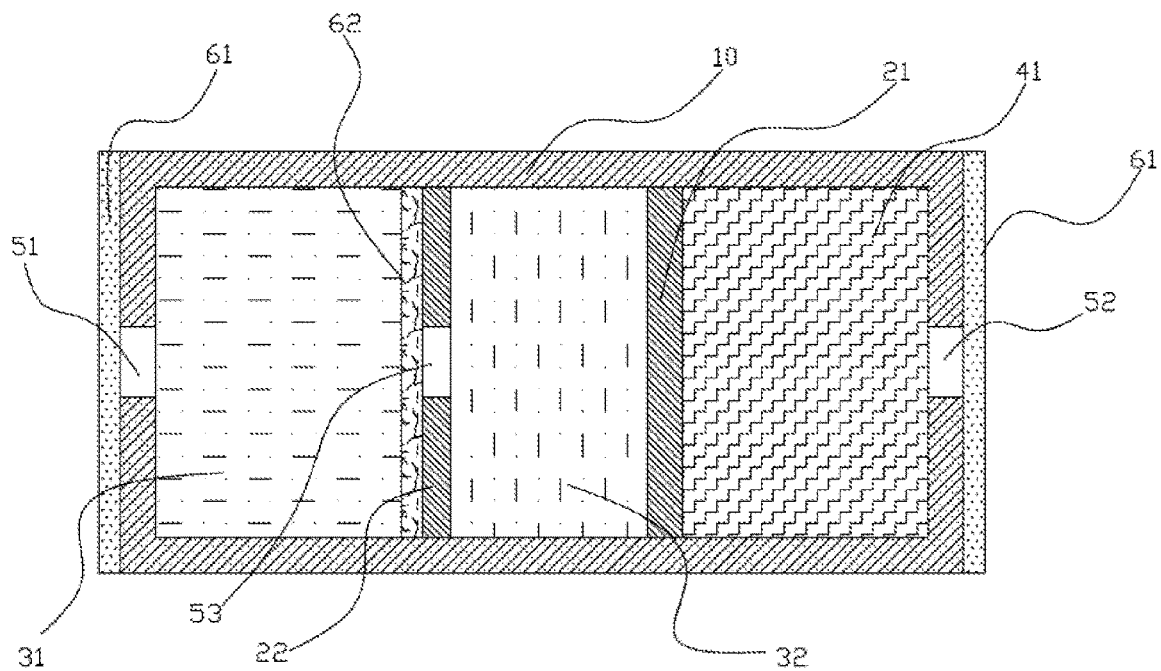
FIG. 4 shows a structural view of an automatic drug delivery device according to the second embodiment of the present invention.
Figure 5:
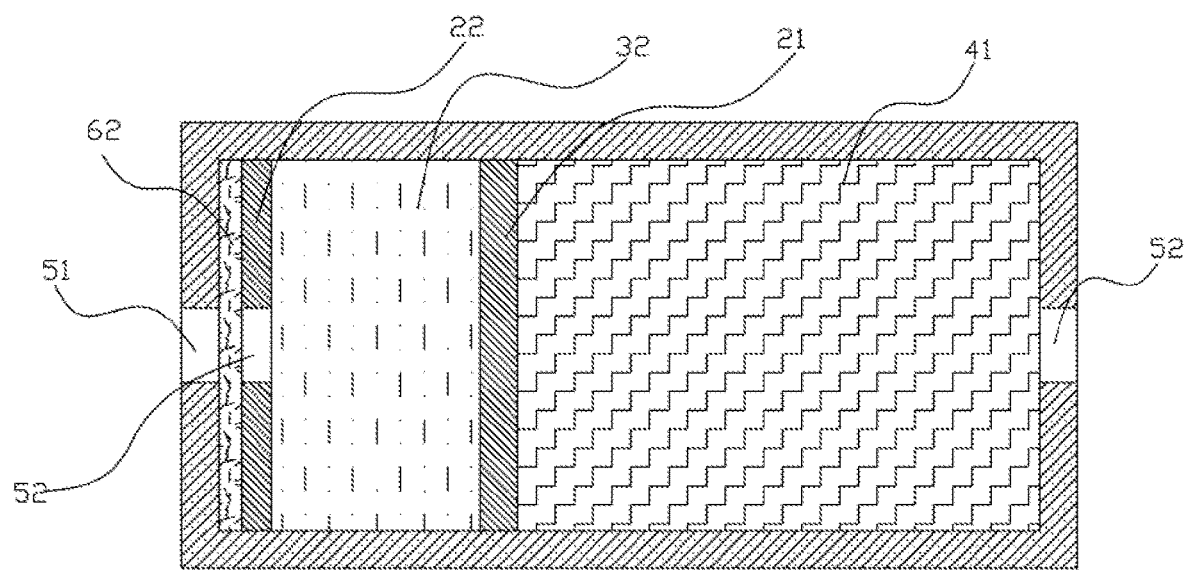
FIG. 5 shows a structural view of the automatic drug delivery device of FIG. 4 after drugs in the first drug delivery chamber have been released.
Figure 6:
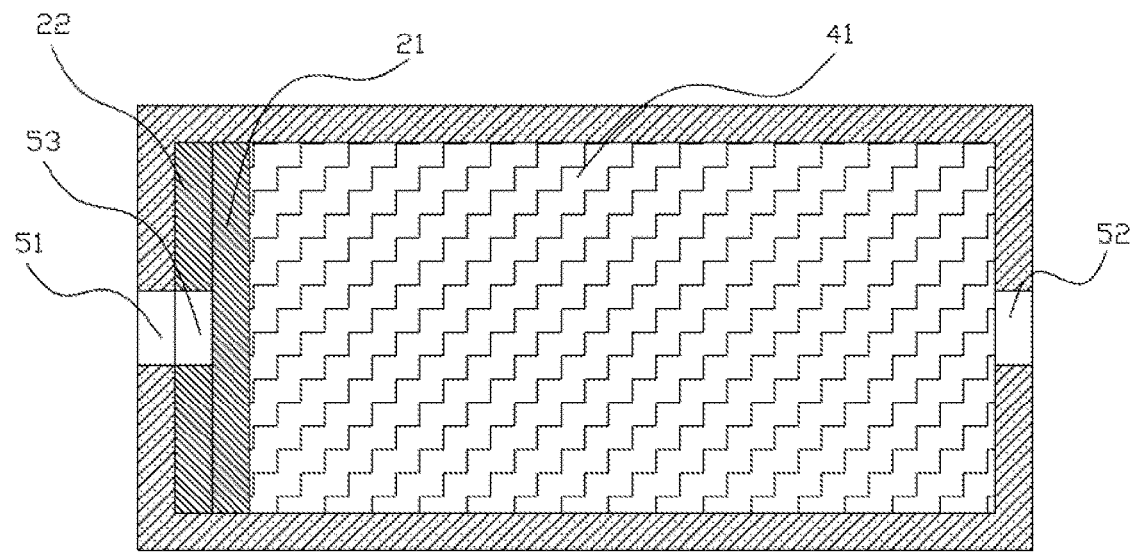
FIG. 6 shows a structural view of the automatic drug delivery device of FIG. 4 after drugs in the second drug delivery chamber have been released.

FIG. 4 shows a structural view of an automatic drug delivery device according to the second embodiment of the present invention. FIG. 5 shows a structural view of the automatic drug delivery device of FIG. 4 after drugs in the first drug delivery chamber have been released. FIG. 6 shows a structural view of the automatic drug delivery device of FIG. 4 after drugs in the second drug delivery chamber have been released. Referring to FIGS. 4-6, the automatic drug delivery device according to the second embodiment of the present invention is basically the same as the automatic drug delivery device according to the first embodiment, except that the automatic drug delivery device further comprises a second drug delivery chamber 32. A second piston 22 is disposed between the first drug delivery chamber 31 and the second drug delivery chamber 32. The first drug delivery chamber 31 is disposed in a side of the second drug delivery chamber 32 opposite the first expansion chamber 41. A third through hole 53 is formed in the second piston 22, and the third through hole 53 is covered by a second targeted dissolution membrane 62 that dissolves at a second targeted region.

Referring to FIGS. 4~6, in the embodiment, both the first drug delivery chamber 31 and the second drug delivery chamber 32 are filled with drugs. The drugs in the first drug delivery chamber 31 and the second drug delivery chamber 32 can be the same or different. When the automatic drug delivery device according to the embodiment reaches the first targeted region, the first targeted dissolution membrane 61 on the first through hole 51 and the second through hole 52 is dissolved, and the expandable material in the first expansion chamber 41 can push the first piston 21 and the second piston 22 to release the drug in the first drug delivery chamber 31. Since the environment at the first targeted region cannot dissolve the second targeted dissolution membrane 62, the drug in the second drug delivery chamber 32 can not be released. When the automatic drug delivery device reaches the second targeted region, the second targeted dissolution membrane 62 dissolves, and the expandable material in the first expansion chamber 41 continues to expand, pushing the first piston 21, to release the drug in the second drug delivery chamber 32 through the third through hole 53 and the first through hole 51.

The automatic drug delivery device according to the embodiment enables release of drugs at a plurality of regions in the digestive tract, which is simple and convenient.

Figure 7:
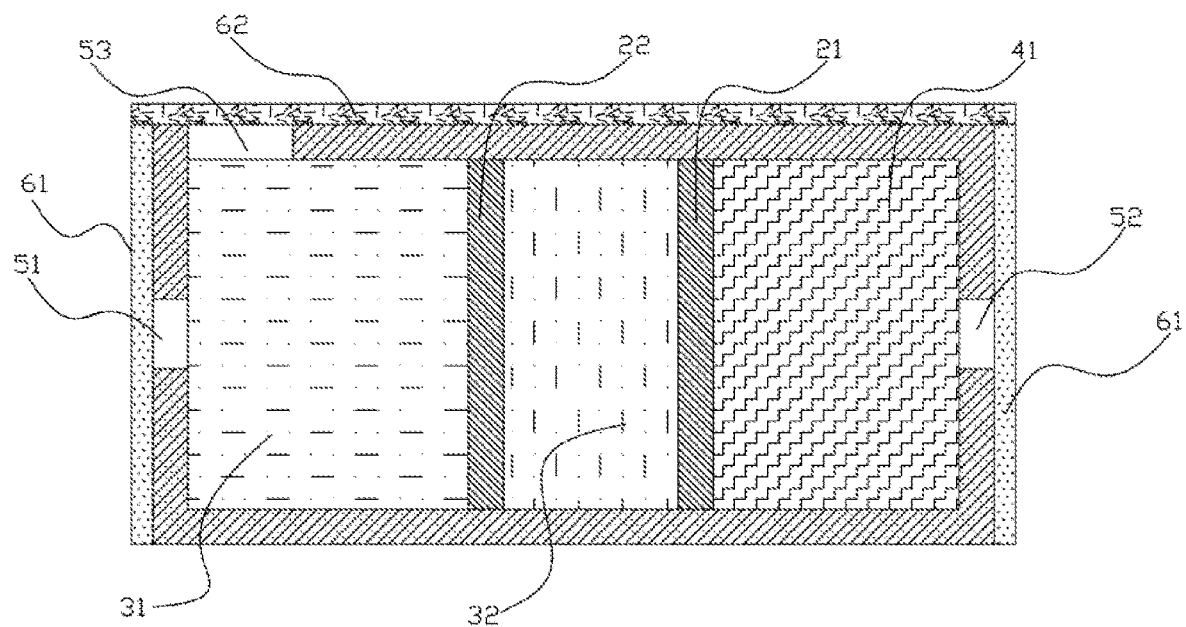
FIG. 7 shows a structural view of an automatic drug delivery device according to the third embodiment of the present invention.

FIG. 7 shows a structural view of an automatic drug delivery device according to the third embodiment of the present invention. The automatic drug delivery device according to the third embodiment of the present invention is basically the same as the second embodiment, and it also comprises a second drug delivery chamber 32, and a second piston 22 is also disposed between the first drug delivery chamber 31 and the second drug delivery chamber 32. In the embodiment, the difference is that the third through hole 53 is formed in the wall of the enclosure 10, and covered with a second targeted dissolution membrane 62. After the drug in the first drug delivery chamber 31 is released, the third through hole 53 communicates with the second drug delivery chamber 32 as the second drug delivery chamber 32 moves.

In the embodiment, since the third through hole 53 communicates with the second drug delivery chamber 32 only after the drug in the first drug delivery chamber 31 is released, it can effectively prevent the drug in the second drug delivery chamber 32 from being released in advance.

Figure 8:
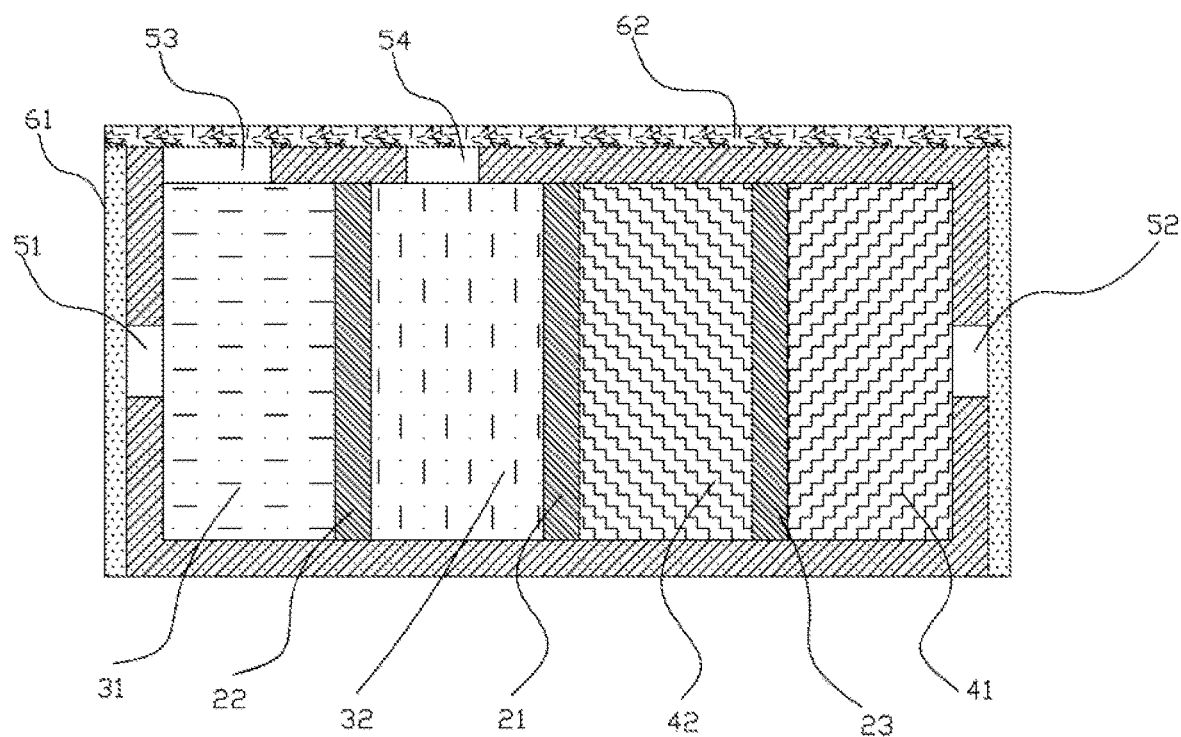
FIG. 8 shows a structural view of an automatic drug delivery device according to the fourth embodiment of the present invention.

FIG. 8 shows a structural view of an automatic drug delivery device according to the fourth embodiment of the present invention. Referring to FIG. 8, the automatic drug delivery device according to the fourth embodiment of the present invention is basically the same as the third embodiment. The difference is that the automatic drug delivery device further comprises a second expansion chamber 42. The second expansion chamber 42 comprises a an expandable material that can absorb liquid to expand. A third piston 23 is disposed between the first expansion chamber 41 and the second expansion chamber 42, and the second expansion chamber 42 is disposed in a side of the first expansion chamber 41 opposite the second through hole 52. In an preferred embodiment, a fourth through hole 54 is formed in the wall of the enclosure 10 of the automatic drug delivery device, and the fourth through hole 54 is covered by a second targeted dissolution membrane 62. After the drug in the first drug delivery chamber 31 is released, as the first piston 21, the second piston 22, and the third piston 23 move, the third through hole 53 communicates with the second drug delivery chamber 32, and the fourth through hole 54 communicates with the second expansion chamber 42.

When the automatic drug delivery device reaches a first targeted region, the first targeted dissolution membrane 61 dissolves, and the liquid at the targeted region enters the first expansion chamber 41, wherein the expandable material in the first expansion chamber 41 absorbs the liquid to expand, pushing the first piston 21, the second piston 22 and the third piston 23 to release the drug in the first drug delivery chamber 31. As the first piston 21, the second piston 22, and the third piston 23 move, the third through hole 53 communicates with the second drug delivery chamber 32, and the fourth through hole 54 communicates with the second expansion chamber 42. When the automatic drug delivery device reaches a second targeted region, the second targeted dissolution membrane 62 dissolves, and the liquid at the targeted region enters the second expansion chamber 42, wherein the expandable material in the second expansion chamber 42 absorbs the liquid to expand, compressing the second drug delivery chamber 32 to release the drug therein.

The automatic drug delivery device according to the embodiment can prevent the expandable material in the first expansion chamber 41 from expanding excessively at the first targeted region, which may cause the second targeted dissolution membrane to break due to over pressure in the second drug delivery chamber 32, so that the automatic drug delivery device can accurately release drug in the second drug delivery chamber 32 at the correct region.

In the above embodiment, the second piston 22 and the third piston 23 can be made of one or more of styrene-butadiene rubber, ethylene-propylene-diene rubber, silicone rubber, polyurethane rubber, and nitrile rubber.

In summary, the present invention provides a piston, an expandable material and a targeted dissolving material, which are arranged to enable the targeted dissolving material to dissolve at a targeted region and then the expandable material absorbs liquid to expand and push the piston to release the drug at a targeted position. The present invention provides an automatic drug delivery device that can automatically release drug at a targeted region without an external power source, and can better control the drug release rate.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. An automatic drug delivery device, comprising:
   an enclosure, continuously covering the automatic drug delivery device along both horizontal and vertical dimensions, and a first piston disposed in the enclosure, wherein the first piston partitions the enclosure to a first drug delivery chamber and a first expansion chamber;
   a first through hole and a second through hole formed in a wall of the enclosure, wherein the first through-hole communicates with the first drug delivery chamber, and the second through-hole communicates with the first expansion chamber, both the first and second through hole are positioned on the vertical dimension, shorter dimension, of the automatic drug delivery device, and length of the first and second through holes is substantially less than the enclosure therein, along the same vertical dimension;
   a first targeted dissolution membrane, which covers the first through hole and the second through hole and dissolves at a first targeted region, configured to expose the first and second through holes after dissolution;
   a drug filled in the first drug delivery chamber; and
   an expandable material provided in the first expansion chamber, that can expand after absorbing liquid,
   a second drug delivery chamber;
   a second piston provided between the first drug delivery chamber and the second drug delivery chamber, wherein the first drug delivery chamber is disposed on a side of the second drug delivery chamber opposite the first expansion chamber;
   a third through hole communicating with the second drug delivery chamber;
   a second targeted dissolution membrane covering the third through hole that dissolves at a second targeted region; and
   the first drug in the first drug delivery chamber and the second drug in the second drug delivery chamber;
   wherein a first drug in the first drug delivery chamber and a second drug in the second drug delivery chamber are different, and the first targeted dissolution membrane and the second targeted dissolution membrane are configured to dissolve in different targeted regions.

2. The automatic drug delivery device of claim 1, wherein an expansion rate of the expandable material that absorbs liquid and/or a size of the second through hole are controlled to adjust a compression rate of the first drug delivery chamber by the first piston, so as to control the drug release rate.

3. The automatic drug delivery device of claim 1, wherein the third through hole is formed in the second piston, and the third through hole communicates with the second drug delivery chamber.

4. The automatic drug delivery device of claim 1, wherein the third through hole is formed in the wall of the enclosure, and when the drug in the first drug delivery chamber is released, the third through hole communicates with the second drug delivery chamber.

5. The automatic drug delivery device of claim 1, wherein the automatic drug delivery device further comprises:
   a second expansion chamber;
   a second expandable material disposed in the second expansion chamber, that expands after absorbing liquid;
   a third piston provided between the first expansion chamber and the second expansion chamber;
   a fourth through hole that is covered by the second targeted dissolution membrane; and
   wherein when the drug in the first drug delivery chamber is released, the third through hole communicates with the second drug delivery chamber and the fourth through hole communicates with the second expansion chamber.

6. The automatic drug delivery device of claim 5, wherein both the third through hole and the fourth through hole are formed in the wall of the enclosure.

7. The automatic drug delivery device of claim 1, wherein the expandable material is water swellable sponge, sodium polyacrylate-modified lignocellulose, chitosan-modified lignocellulose, or a polymer mixed by rubber polymer with water-absorbing resin.

8. The automatic drug delivery device of claim 5, wherein the expandable material is water swellable sponge, sodium polyacrylate-modified lignocellulose, chitosan-modified lignocellulose, or a polymer mixed by rubber polymer with water-absorbing resin.

9. The automatic drug delivery device of claim 1, wherein the first targeted dissolution membrane and the second targeted dissolution membrane are selected from a mixture of EUDRAGIT L100-55 and EUDRAGIT Plastoid B, pectin, guar gum, or a mixture of EUDRAGIT S100 and EUDRAGIT Plastoid B.

10. The automatic drug delivery device of claim 1, wherein the enclosure is made of one or more of medical grade polycarbonate, polyurethane, polyacrylate, polymethyl methacrylate, polyetheretherketone, polystyrene and polyethylene.

11. The automatic drug delivery device of claim 1, wherein the first targeted dissolution membrane extends an additional 0.5-1 cm at each corner of the first through hole.

* * * * *